United States Patent
Ziv

(10) Patent No.: US 8,715,195 B2
(45) Date of Patent: May 6, 2014

(54) SYSTEM AND METHOD FOR ACCURATE PLACEMENT OF A CATHETER TIP IN A PATIENT

(75) Inventor: David Ziv, Merom Ha-Galil (IL)

(73) Assignee: Elcam Medical Agricultural Cooperative, Merom Ha-Galil (IL)

( * ) Notice: Subject to any disclaimer, the term of this patent is extended or adjusted under 35 U.S.C. 154(b) by 696 days.

(21) Appl. No.: 12/594,869

(22) PCT Filed: Apr. 9, 2008

(86) PCT No.: PCT/IL2008/000481
§ 371 (c)(1),
(2), (4) Date: Nov. 10, 2009

(87) PCT Pub. No.: WO2008/126074
PCT Pub. Date: Oct. 23, 2008

(65) Prior Publication Data
US 2010/0049062 A1      Feb. 25, 2010

Related U.S. Application Data

(60) Provisional application No. 60/923,160, filed on Apr. 11, 2007.

(51) Int. Cl.
*A61B 5/0215*          (2006.01)

(52) U.S. Cl.
USPC .................. 600/486; 600/500; 600/505

(58) Field of Classification Search
USPC ............. 600/481, 485, 486, 488, 500–507; 604/264, 523, 528
See application file for complete search history.

(56) References Cited

U.S. PATENT DOCUMENTS

| | | |
|---|---|---|
| 3,585,996 A | 6/1971 | Reynolds et al. |
| 4,821,731 A | 4/1989 | Martinelli et al. |
| 5,042,486 A | 8/1991 | Pfeiler et al. |
| 5,078,714 A | 1/1992 | Katims |
| 5,099,845 A | 3/1992 | Besz et al. |

(Continued)

FOREIGN PATENT DOCUMENTS

| | | |
|---|---|---|
| EP | 0091577 | 10/1983 |
| EP | 0775466 | 5/1997 |

(Continued)

OTHER PUBLICATIONS

Schummer W, et al., "ECG-guided central venous catheter positioning: does it detect the pericardial reflection rather than the right atrium?" Eur J Anaesthesiol. Aug. 2004; 21(8): 600-5.

(Continued)

*Primary Examiner* — Patricia Mallari
*Assistant Examiner* — Michael Catina
(74) *Attorney, Agent, or Firm* — Sughrue Mion, PLLC

(57) ABSTRACT

A system for accurate placement of a catheter tip in a patient, the system including a catheter adapted for placement within a patient, the catheter having a tip at a distal end thereof and having a proximal end which is normally located outside of the patient, a pressure sensor adapted to sense pressure at the tip of the catheter and catheter tip placement location indicating circuitry operative in response to at least an output of the pressure sensor for indicating the location of the catheter tip in the patient.

13 Claims, 3 Drawing Sheets

(56) References Cited

U.S. PATENT DOCUMENTS

| | | |
|---|---|---|
| 5,370,640 A | 12/1994 | Kolff |
| 5,375,596 A | 12/1994 | Twiss et al. |
| 5,386,828 A | 2/1995 | Owens et al. |
| 5,425,367 A | 6/1995 | Shapiro et al. |
| 5,431,628 A | 7/1995 | Millar |
| 5,498,239 A | 3/1996 | Galel et al. |
| 5,526,820 A | 6/1996 | Khoury |
| 5,592,939 A | 1/1997 | Martinelli |
| 5,622,169 A | 4/1997 | Golden et al. |
| 5,645,065 A | 7/1997 | Shapiro et al. |
| 5,697,377 A | 12/1997 | Wittkampf |
| 5,727,552 A | 3/1998 | Ryan |
| 5,727,553 A | 3/1998 | Saad |
| 5,749,835 A | 5/1998 | Glantz |
| 5,755,668 A | 5/1998 | Itoigawa et al. |
| 5,769,786 A | 6/1998 | Wiegel |
| 5,843,076 A | 12/1998 | Webster, Jr. et al. |
| 5,860,938 A | 1/1999 | Lafontaine et al. |
| 5,899,860 A | 5/1999 | Pfeiffer et al. |
| 5,904,657 A | 5/1999 | Unsworth et al. |
| 5,951,497 A | 9/1999 | Wallace et al. |
| 5,964,714 A | 10/1999 | Lafontaine |
| 5,983,126 A | 11/1999 | Wittkampf |
| 6,006,123 A | 12/1999 | Nguyen et al. |
| 6,038,468 A | 3/2000 | Rex |
| 6,052,610 A | 4/2000 | Koch |
| 6,061,588 A | 5/2000 | Thornton et al. |
| 6,073,043 A | 6/2000 | Schneider |
| 6,120,457 A | 9/2000 | Coombes et al. |
| 6,226,546 B1 | 5/2001 | Evans |
| 6,230,042 B1 | 5/2001 | Slettenmark |
| 6,298,261 B1 | 10/2001 | Rex |
| 6,304,769 B1 | 10/2001 | Arenson et al. |
| 6,394,986 B1 | 5/2002 | Millar |
| 6,398,738 B1 | 6/2002 | Millar |
| 6,447,458 B1* | 9/2002 | Farrell et al. .................. 600/500 |
| 6,616,597 B2 | 9/2003 | Schock et al. |
| 6,618,612 B1 | 9/2003 | Acker et al. |
| 6,647,287 B1* | 11/2003 | Peel et al. ...................... 600/513 |
| 6,671,550 B2* | 12/2003 | Iaizzo et al. ..................... 607/27 |
| 6,690,963 B2 | 2/2004 | Ben-Haim et al. |
| 6,711,429 B1 | 3/2004 | Gilboa et al. |
| 6,741,883 B2 | 5/2004 | Gildenberg |
| 6,834,201 B2 | 12/2004 | Gillies |
| 6,892,091 B1 | 5/2005 | Ben-Haim et al. |
| 6,974,422 B1 | 12/2005 | Millar |
| 6,977,504 B2 | 12/2005 | Wright et al. |
| 7,197,349 B2 | 3/2007 | Taimisto et al. |
| 7,197,354 B2 | 3/2007 | Sobe |
| 7,505,808 B2 | 3/2009 | Anderson et al. |
| 2002/0007125 A1 | 1/2002 | Hickey |
| 2002/0165448 A1 | 11/2002 | Ben-Haim et al. |
| 2004/0006268 A1 | 1/2004 | Gilboa et al. |
| 2004/0019447 A1 | 1/2004 | Shachar |
| 2004/0097804 A1 | 5/2004 | Sobe |
| 2004/0147837 A1 | 7/2004 | Macaulay et al. |
| 2004/0153109 A1 | 8/2004 | Tiedtke et al. |
| 2004/0242995 A1 | 12/2004 | Maschke |
| 2005/0054918 A1 | 3/2005 | Sra |
| 2005/0113685 A1 | 5/2005 | Maschke et al. |
| 2005/0119708 A1 | 6/2005 | Haefner |
| 2005/0256398 A1 | 11/2005 | Hastings et al. |
| 2006/0030833 A1 | 2/2006 | Harris et al. |
| 2006/0116572 A1 | 6/2006 | Case |
| 2006/0247522 A1 | 11/2006 | McGee |
| 2006/0253160 A1* | 11/2006 | Benditt et al. .................. 607/17 |
| 2006/0281990 A1 | 12/2006 | Viswanathan et al. |
| 2006/0287604 A1* | 12/2006 | Hickey ........................... 600/508 |
| 2007/0016006 A1 | 1/2007 | Shachar et al. |
| 2007/0032723 A1 | 2/2007 | Glossop |
| 2007/0049818 A1 | 3/2007 | Hirakawa et al. |
| 2007/0135713 A1 | 6/2007 | Borgert et al. |
| 2007/0167813 A1 | 7/2007 | Lee et al. |
| 2007/0197899 A1 | 8/2007 | Ritter et al. |
| 2007/0232896 A1 | 10/2007 | Gilboa et al. |
| 2007/0276216 A1 | 11/2007 | Beyar et al. |
| 2007/0282197 A1 | 12/2007 | Bill et al. |
| 2007/0287909 A1 | 12/2007 | Garibaldi et al. |
| 2008/0009711 A1 | 1/2008 | Govari et al. |
| 2008/0097232 A1 | 4/2008 | Rothenberg |
| 2008/0108901 A1 | 5/2008 | Baba et al. |
| 2008/0146942 A1 | 6/2008 | Dala-Krishna |
| 2008/0161681 A1 | 7/2008 | Hauck |
| 2008/0177174 A1 | 7/2008 | Crane |
| 2008/0183071 A1 | 7/2008 | Strommer et al. |
| 2008/0221435 A1 | 9/2008 | Rasche |
| 2008/0249395 A1 | 10/2008 | Shachar et al. |
| 2008/0255475 A1 | 10/2008 | Kondrosky et al. |
| 2008/0294034 A1 | 11/2008 | Krueger et al. |
| 2009/0062641 A1 | 3/2009 | Barbu et al. |
| 2009/0088632 A1 | 4/2009 | Khamene et al. |
| 2009/0088648 A1 | 4/2009 | Jaffe et al. |
| 2009/0118620 A1 | 5/2009 | Tgavalekos et al. |

FOREIGN PATENT DOCUMENTS

| | | |
|---|---|---|
| EP | 0973454 | 1/2000 |
| EP | 1322377 | 7/2003 |
| JP | 2002 153443 | 5/2002 |
| WO | WO 96/28800 | 9/1996 |
| WO | WO 00/68637 | 11/2000 |
| WO | WO 2007/015180 | 2/2007 |
| WO | WO 2008/017999 | 2/2008 |
| WO | WO 2008/126074 | 10/2008 |
| WO | WO 2009/070616 | 6/2009 |

OTHER PUBLICATIONS

Schummer W, et al., "Intra-atrial ECG is not a reliable method for positioning left internal jugular vein catheters", Br J Anaesth. Oct. 2003; 91(4): 481-6.

Madias JE, "Intracardiac (superior vena cava/right atrial) ECGs using saline solution as the conductive medium for the proper positioning of the Shiley hemodialysis catheter: is it not time to forego [correction of forgo] the postinsertion chest radiograph?", Chest. Dec. 2003; 124(6):2363-7.

Work J., "Chronic catheter placement", Semin Dial. Nov.-Dec. 2001; 14(6): 436-40.

* cited by examiner

SYSTEM AND METHOD FOR ACCURATE PLACEMENT OF A CATHETER TIP IN A PATIENT

REFERENCE TO RELATED APPLICATIONS

The present application is related to U.S. Provisional Patent Application Ser. No. 60/923,160, filed Apr. 11, 2007 and entitled CATHFINDER, the disclosure of which is hereby incorporated by reference and priority of which is hereby claimed pursuant to 37 CFR 1.78(a) (4) and (5)(i).

FIELD OF THE INVENTION

The present invention relates to medical devices and methodologies generally and more particularly to devices and methodologies for accurate catheter tip placement in a patient.

BACKGROUND OF THE INVENTION

The following patent documents are believed to represent the current state of the art:

U.S. Pat. Nos. 3,585,996; 4,821,731; 5,042,486; 5,078,714; 5,099,845; 5,370,640; 5,375,596; 5,386,828; 5,425,367; 5,498,239; 5,526,820; 5,592,939; 5,622,169; 5,727,552; 5,727,553; 5,749,835; 5,755,668; 5,843,076; 5,860,938; 5,899,860; 5,904,657; 5,983,126; 6,038,468; 6,052,610; 6,073,043; 6,226,546; 6,230,042; 6,298,261; 6,304,769; 6,618,612; 6,690,963; 6,711,429; 6,741,883 and 7,197,354;

U.S. Published Patent Application Nos. 2002/0165448; 2004/0006268; 2004/0097804; 2004/0019447; 2004/0147837; 2005/0256398; 2006/0030833; 2006/0116572; 2006/0247522; 2006/0281990; 2007/0016006; 2007/0032723; 2007/0135713; 2007/0197899; 2007/0232896; 2007/0276216; 2007/0282197; 2007/0287909 and 2008/0009711;

Published PCT Patent Application Nos. WO 00/068637A1 and WO 07/015180A1; and

European Patent No. EP 1,322,377.

SUMMARY OF THE INVENTION

The present invention seeks to provide an improved system and methodology for accurate placement of a catheter tip inside a patient.

There is thus provided in accordance with a preferred embodiment of the present invention a system for accurate placement of a catheter tip in a patient, the system including a catheter adapted for placement within a patient, the catheter having a tip at a distal end thereof and having a proximal end which is normally located outside of the patient, a pressure sensor adapted to sense pressure at the tip of the catheter and catheter tip placement location indicating circuitry operative in response to at least an output of the pressure sensor for indicating the location of the catheter tip in the patient.

Preferably, the catheter tip placement location indicating circuitry is operative in response additionally to an ECG signal.

In accordance with a preferred embodiment of the present invention, the pressure sensor is adapted to sense a heart valve opening/closing signal which propagates at approximately 1540 m/sec. and to sense a pressure wave that is generating by the emptying, filling and contraction of the right atrium which propagates at approximately 2 m/sec. Additionally, the catheter tip placement location indicating circuitry is operative to distinguish between the heart valve opening/closing signal and the pressure wave that is generating by the emptying, filling and contraction of the right atrium. Additionally or alternatively, the catheter tip placement location indicating circuitry is operative for indicating the location of the catheter tip in the patient on the basis of the time relationship of the heart valve opening/closing signal and the pressure wave that is generating by the emptying, filling and contraction of the right atrium sensed by the pressure sensor.

Preferably, the pressure sensor is located at the catheter tip. Alternatively, the pressure sensor is located at the proximal end of the catheter.

In accordance with a preferred embodiment of the present invention, the catheter tip placement location indicating circuitry is operative to provide an indication that the catheter tip is located in the patient at the junction of the superior vena cava (SVC) and the right atrium (RA). Additionally, the indication is based on the change in successive measurements of a propagation delay in pressure waves measured by the pressure sensor.

Preferably, the system also includes a computer operative to provide catheter tip insertion instructions based at least partially on an output from the catheter tip placement location indicating circuitry.

There is also provided in accordance with another preferred embodiment of the present invention a method for accurate placement of a catheter tip in a patient, the method including placing a catheter within a patient, the catheter having a tip at a distal end thereof and having a proximal end which is normally located outside of the patient, sensing pressure at the tip of the catheter and indicating the location of the catheter tip in the patient based at least partially on an output of the sensing.

Preferably, the indicating is also based at least partially on an ECG signal.

In accordance with a preferred embodiment of the present invention, the sensing pressure includes sensing a heart valve opening/closing signal which propagates at approximately 1540 m/sec. and sensing a pressure wave generated by the emptying, filling and contraction of the right atrium which propagates at approximately 2 m/sec. Additionally, the method for accurate placement of a catheter tip in a patient also includes distinguishing between the heart valve opening/closing signal and the pressure wave. Additionally, the indicating includes calculating a time relationship between the heart valve opening/closing signal and the pressure wave.

Preferably, the indicating includes providing an indication that the tip is located in the patient at the junction of the superior vena cava (SVC) and the right atrium (RA). Additionally or alternatively, the method also includes providing catheter tip insertion instructions based at least partially on an output from the indicating.

BRIEF DESCRIPTION OF THE DRAWINGS

The present invention will be understood and appreciated more fully from the following detailed description, taken in conjunction with the drawings in which.

DETAILED DESCRIPTION OF PREFERRED EMBODIMENTS

The present invention provides a system and methodology for accurate placement of a catheter tip in a patient employing a catheter adapted for placement within a patient, the catheter having a tip at a distal end thereof and having a proximal end which is normally located outside of the patient, a pressure sensor adapted to sense pressure at said tip of the catheter and catheter tip placement location indicating circuitry operative in response to at least an output of the pressure sensor for indicating the location of the catheter tip in the patient.

Although the present invention is not limited in its application to cardiac applications, it is particularly useful in such applications and therefore, for reasons of clarity of explanation, is described hereinbelow with reference to placement of a catheter tip near or at the heart, it being appreciated that other applications are also envisaged.

Figure 1:
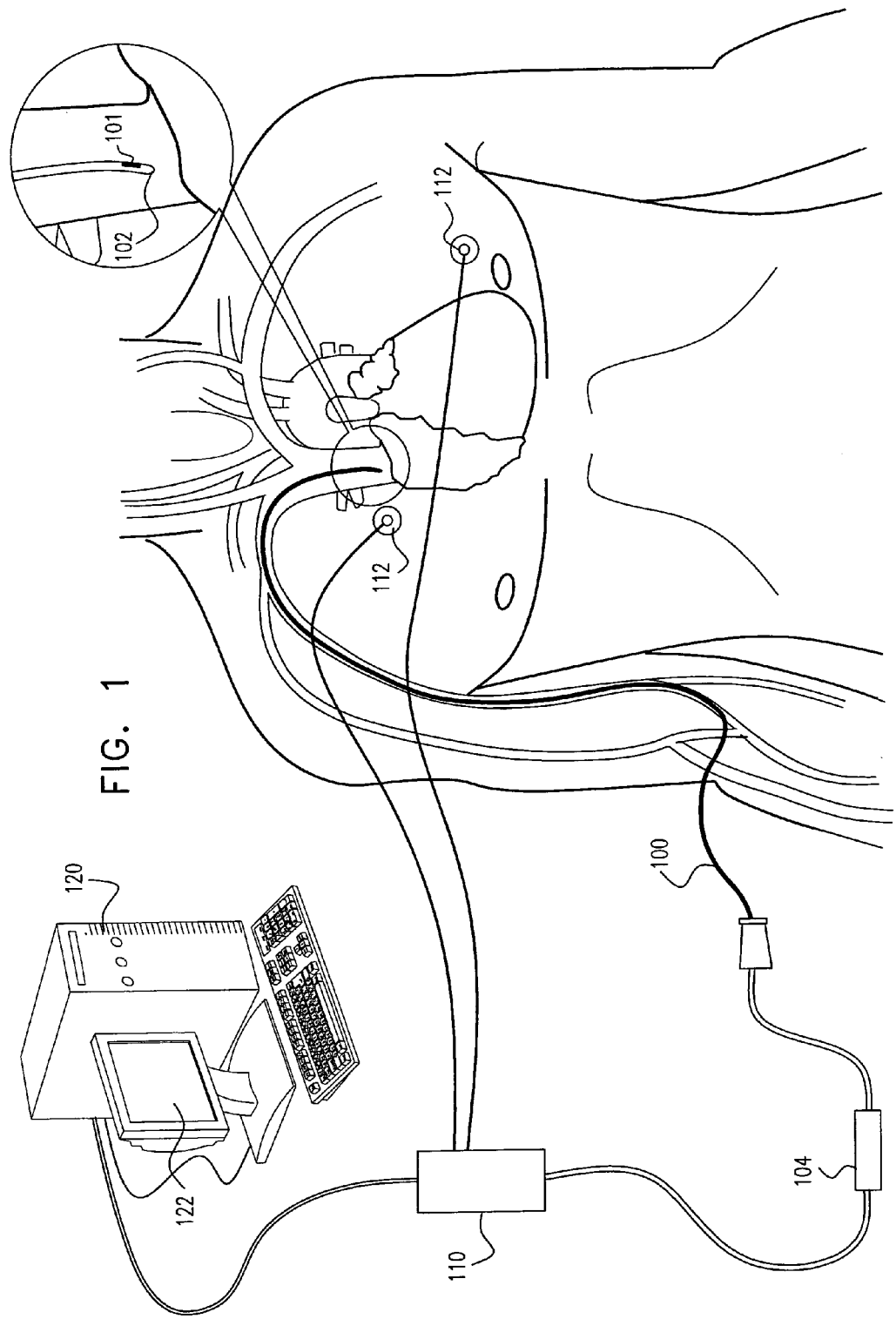
FIG. 1 is a simplified illustration of a system for accurate placement of a catheter tip inside a patient constructed and operative in accordance with a preferred embodiment of the present invention.

Reference is now made to FIG. 1, which is a simplified block diagram illustration of a system for accurate placement of a catheter tip inside a patient constructed and operative in accordance with a preferred embodiment of the present invention. In the embodiment of FIG. 1, a catheter 100, such as a Morpheus® 5F Dual Lumen CT PICC, Cat. No. 12100813, commercially available from AngioDynamics, Inc., 603 Queensbury Ave., Queensbury, N.Y., USA, having a pressure sensor 101 at its tip 102 is shown inserted into a vein of a patient, such that the tip 102 is in the vicinity of the right atrium. Alternatively, as shown in FIG. 1, a pressure sensor 104 may be connected to a proximal end of catheter 100, which may be a catheter such as a Straight Transducer MM, Cat. No. 650101, commercially available from Elcam Medical, Baram, Israel.

The pressure sensor 101 or 104, irrespective of its location either at the tip 102 or at the proximal end of catheter 100 respectively, preferably senses a venous pressure waveform, including at least one of, and preferably both, a V pressure wave, generated by filling of the right atrium, and an A pressure wave, generated by contraction of the right atrium, both of which propagate at approximately 2 m/sec. along a large vein.

Preferably, pressure sensor 101 or 104 also senses acoustic pressure waves generated by opening and closing of one or more of the heart valves, which propagate at approximately 1540 m/sec. in soft biological tissue. The rapid propagation of the acoustic pressure waves generated by the opening and closing of the heart valves relative to the propagation of the V and A pressure waves in the blood along a vein results in a propagation delay that is negligible relative to the delay of the propagation of the V and A pressure waves.

An output of the pressure sensor 101 or 104 is preferably supplied to catheter tip placement location indicating circuitry 110, which is operative to indicate the location of the catheter tip 102 in the patient based on the propagation delay of the V and/or the A pressure waves generated by the respective filling and contraction of the right atrium sensed by pressure sensor 101 or 104, relative to the rapidly propagating pressure waves generated by the opening and closing of the heart valves sensed by the pressure sensor 101 or 104.

As seen in FIG. 1, optionally ECG transducers 112 may be placed on the patient and coupled to the catheter tip placement location indicating circuitry 110. The ECG R wave may be employed by the catheter tip placement location indicating circuitry 110 in place of, or in addition to, the acoustic pressure waves generated by opening and closing of the heart valves, sensed by pressure sensor 101 or 104, as a fiducial point with respect to which the propagation delay of the V and/or A pressure waves may be measured.

One or more outputs of catheter tip placement location indicating circuitry 110 may be provided to a computer 120 which preferably has associated therewith a monitor 122. Monitor 122 may display one or more of the A and V waves, pressure waves generated by opening and closing of the heart valves, and ECG R wave, and preferably also provides a visual display indicating the location of the catheter tip 102.

Figure 2:
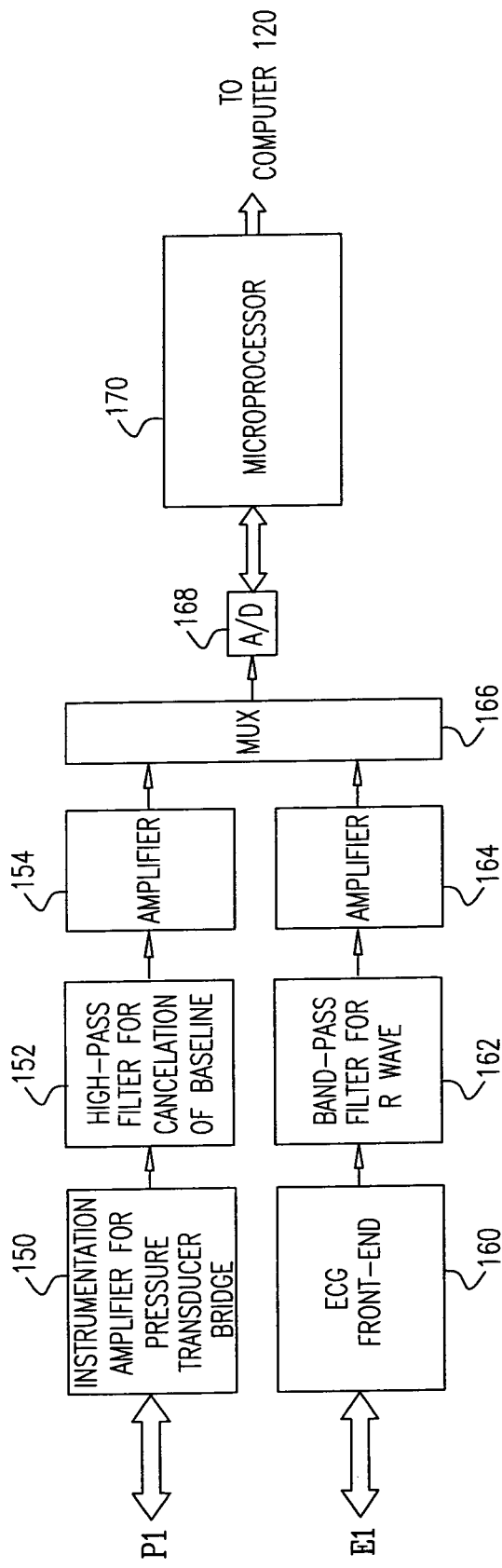
FIG. 2 is a simplified block diagram illustration of part of one embodiment of a system for accurate placement of a catheter tip inside a patient.

It is appreciated that computer 120 may also include hardware and/or software operative to provide, for example by displaying on monitor 122, catheter tip insertion instructions based at least partially on the outputs from circuitry 110, such as procedure specific insertion instructions for placing catheter tip 102 at a specific location within the patient. Reference is now made to FIG. 2, which is a simplified block diagram illustration of catheter tip placement location indicating circuitry, forming part of one embodiment of a system for accurate placement of a catheter tip inside a patient. As seen in FIG. 2, the catheter tip placement location indicating circuitry preferably comprises an instrumentation amplifier for a pressure transducer bridge 150, such as an AD620, commercially available from Analog Devices, Inc., One Technology Way, Norwood, Mass., USA, which receives an input from pressure sensor 101 or 104 (FIG. 1), designated here as P1. The output of the amplifier 150 is preferably supplied via a high-pass filter 152, typically having a pass band of above 8 Hz, to an amplifier 154.

An ECG front end 160, such as an AD620, commercially available from Analog Devices, Inc., One Technology Way, Norwood, Mass., USA, receives outputs, designated here as E1, from ECG transducers 112 (FIG. 1). The output of the ECG front end 160 is preferably supplied via a band-pass filter 162, typically having a lower frequency threshold of 0.5 Hz and a high frequency cutoff frequency of 35 Hz, to an amplifier 164.

A multiplexer 166 preferably receives the outputs of amplifiers 154 and 164 and provides an analog input to an A/D converter 168 which outputs to a microprocessor 170, which is operative to differentiate the various input waves and ascertain their time relationship, by considering time delays along the catheter, as well as time delays in the various amplifiers and filters, thereby to provide an output indication of the location of the tip 102 of the catheter 100. This output indication may be provided to computer 120 (FIG. 1) for possible further processing and for display of relevant data to a clinician at monitor 122 (FIG. 1).

It is appreciated that in this embodiment of the present invention, the ECG R wave may be employed instead of, or in addition to, the pressure waves generated by opening and closing of the heart valves, sensed by pressure sensor 101 or 104 (FIG. 1), as a fiducial point with respect to which the propagation delay of the V and/or A pressure waves may be measured.

Figure 3:
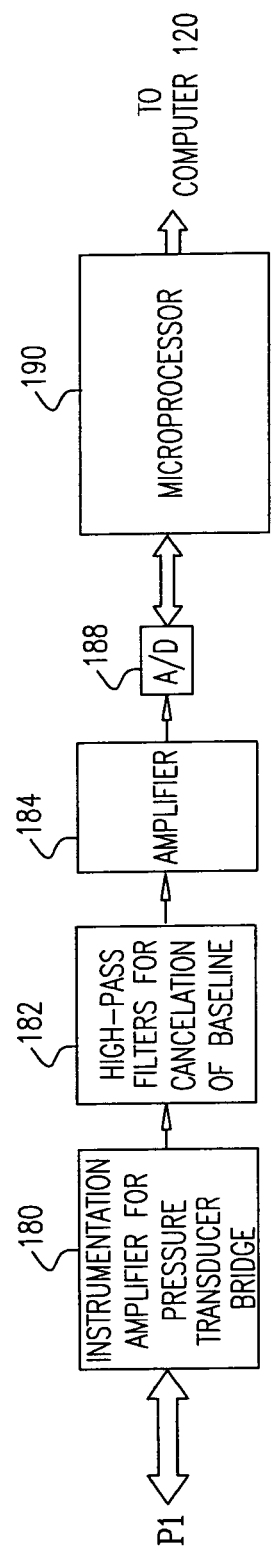
FIG. 3 is a simplified block diagram illustration of part of another embodiment of a system for accurate placement of a catheter tip inside a patient.

Reference is now made to FIG. 3, which is a simplified block diagram illustration of catheter tip placement location indicating circuitry, forming part of one embodiment of a system for accurate placement of a catheter tip inside a patient. As seen in FIG. 3, the catheter tip placement location indicating circuitry preferably comprises an instrumentation amplifier for a pressure transducer bridge 180, such as an AD620, commercially available from Analog Devices, Inc., One Technology Way, Norwood; Mass., USA, which receives an input from pressure sensor 101 or 104 (FIG. 1), designated here as P1. The output of the amplifier 180 is preferably supplied via a high-pass filter 182, typically having a pass band of above 8 Hz, to an amplifier 184.

The output of amplifier 184 is supplied as an analog input to an A/D converter 188 which outputs to a microprocessor 190, which is operative to differentiate the various input waves and ascertain their time relationship, thereby to provide an output indication of the location of the tip 102 of the catheter 100. This output indication may be provided to computer 120 (FIG. 1) for possible further processing and for display of relevant data to a clinician at monitor 122 (FIG. 1).

It is appreciated that in this embodiment of the present invention, the ECG R wave is not employed but rather the acoustic pressure waves generated by opening and closing of the heart valves, sensed by the pressure sensor 101 or 104, are employed to define a fiducial point with respect to which the propagation delay of the V and/or A pressure waves may be measured.

Figure 4:
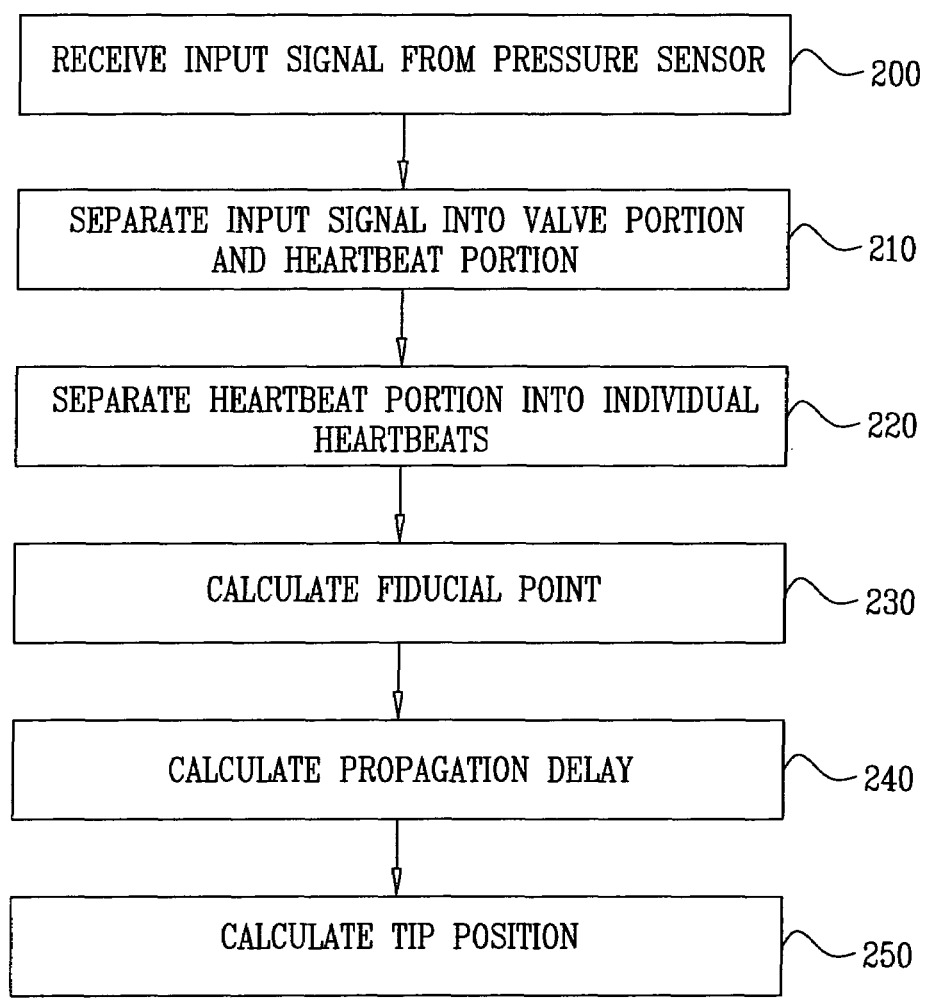
FIG. 4 is a simplified flow chart of an algorithm preferably employed by the system and methodology of FIGS. 1-3.

Reference is now made to FIG. 4, which is a simplified flow chart of an algorithm preferably employed by the system and methodology of FIGS. 1-3. The algorithm is preferably embodied in the operation of microprocessor 170 (FIG. 2) or microprocessor 190 (FIG. 3)

As seen in FIG. 4, the algorithm preferably includes the following steps:

As seen in step 200, an input signal is received from pressure sensor 101 or 104 (FIG. 1). As described hereinabove with reference to FIG. 1, the input signal preferably includes at least a valve sensing portion and a heartbeat sensing portion. The valve sensing portion preferably includes acoustic pressure waves generated by opening and closing of the heart valves, which propagate at approximately 1540 m/sec. in soft biological tissue. The heartbeat portion includes at least one of, and preferably both, the V pressure wave, generated by filling of the right atrium, and the A pressure wave, generated by contraction of the right atrium, both of which propagate at approximately 2 m/sec. inside and along a large vein, or at up to 5 m/sec. in other blood vessels.

In step 210, the input signal received in step 200 is separated into the valve sensing portion and the heartbeat sensing portion, preferably by frequency band. It is appreciated that the valve sensing portion of the signal includes valve closing sounds and/or valve opening sounds which are characterized by lying in a frequency band above 8 Hz and the heartbeat sensing portion of the signal includes the A pressure wave and/or the V pressure wave which are characterized by lying in a frequency band of 0.1-8 Hz.

In step 220, the heartbeat sensing portion of the signal is separated into individual heartbeat signals by using an autocorrelation function or other suitable function applied to either the ECG signal or the valve sensing portion of the signal, or both, to detect individual heartbeat signals and to detect positive zero crossing of the A pressure wave.

Step 230 includes the calculation of a fiducial point against which propagation delay of the A pressure waves and/or the V pressure waves is to be measured. This typically includes averaging the individual heartbeat signals over a predetermined number, typically ten, of heartbeats.

In step 240, the propagation delay of the A pressure wave and/or the V pressure wave relative to the fiducial point is calculated. It is appreciated that the propagation delay may be based on the acoustic waveform of the pressure wave or the ECG waveform or both.

In step 250, the tip position is calculated, typically as a function of the propagation delay and the propagation characteristics of the pressure wave. It is appreciated that propagation delay may be different in different patients, and may specifically be a function of age, which is closely correlated to vessel compliance and therefore to the pressure wave propagation velocity along a blood vessel.

In accordance with another preferred embodiment of the present invention, catheter tip placement location indicating circuitry 110 may be operative in response to at least an output of the pressure sensor to provide an indication that the catheter tip is located in the patient at the junction of the superior vena cava (SVC) and the right atrium (RA). In accordance with this embodiment, catheter tip placement location indicating circuitry 110 is operative to calculate the change in the propagation delay between successive measurements thereof. It is appreciated that the change in the propagation delay is relatively constant during an insertion procedure until the catheter tip reaches the SVC-RA junction, at which point the change in the propagation delay approaches zero with further insertion of catheter 100 as the propagation delay becomes virtually constant.

It is appreciated that computer 120 may also include hardware and/or software operative to provide, for example by displaying on monitor 122, catheter tip insertion instructions based at least partially on the outputs from circuitry 110, such as procedure specific insertion instructions for placing catheter tip 102 at a specific location within the patient.

It will be appreciated by persons skilled in the art that the present invention is not limited by what has been particularly shown and described hereinabove. Rather the invention includes both combinations and subcombinations of various features described hereinabove as well as modifications thereof which would occur to persons skilled in the art upon reading the foregoing description and which are not in the prior art.

The invention claimed is:

1. A system for accurate placement of a catheter tip in a patient, the system comprising:
   a catheter adapted for placement within a vein of a patient, the catheter having a tip at a distal end thereof and having a proximal end which is normally located outside of the patient;
   a pressure sensor adapted to sense pressure within the vein of said patient at said tip of said catheter, said pressure sensor being adapted to sense a venous pressure waveform including at least one of a V pressure wave, generated by filling of the right atrium, and an A pressure wave, generated by contraction of the right atrium; and
   catheter tip placement location indicating circuitry operative in response to at least an output of said pressure sensor and an ECG signal to provide an indication that said catheter tip is located in said patient at the junction of the superior vena cava (SVC) and the right atrium (RA),
   an R wave of said ECG signal being employed by said catheter tip placement location indicating circuitry as a fiducial point with respect to which a propagation delay of said venous pressure waveform is measured, said catheter tip placement location indicating circuitry employing said propagation delay to provide said indication that said catheter tip is located at the junction of the superior vena cava (SVC) and the right atrium (RA).

2. A system for accurate placement of a catheter tip in a patient according to claim 1 and wherein said pressure sensor is adapted to sense a heart valve opening/closing signal which propagates at approximately 1540 m/sec. and to sense a pressure wave that is generating by the emptying, filling and contraction of the right atrium which propagates at approximately 2 m/sec.

3. A system for accurate placement of a catheter tip in a patient according to claim 2 and wherein the catheter tip placement location indicating circuitry is operative to distinguish between the heart valve opening/closing signal and the pressure wave that is generating by the emptying, filling and contraction of the right atrium.

4. A system for accurate placement of a catheter tip in a patient according to claim 2 and wherein the catheter tip placement location indicating circuitry is operative for indicating the location of said catheter tip in said patient on the basis of the time relationship of the heart valve opening/closing signal and the pressure wave that is generating by the emptying, filling and contraction of the right atrium sensed by said pressure sensor.

5. A system for accurate placement of a catheter tip in a patient according to claim 1 and wherein said pressure sensor is located at said catheter tip.

6. A system for accurate placement of a catheter tip in a patient according to claim 1 and wherein said pressure sensor is located at said proximal end of said catheter.

7. A system for accurate placement of a catheter tip in a patient according to claim 1 and wherein said indication is based on the change in successive measurements of a propagation delay in pressure waves measured by said pressure sensor.

8. A system for accurate placement of a catheter tip in a patient according to claim 1 and also comprising a computer and a monitor, said computer operative to provide, by displaying on said monitor, catheter tip insertion instructions based at least partially on an output from said catheter tip placement location indicating circuitry.

9. A method for accurate placement of a catheter tip in a patient, the method comprising:
   placing a catheter within a vein of a patient, said catheter having a tip at a distal end thereof and having a proximal end which is normally located outside of the patient;
   sensing pressure within the vein of said patient at said tip of said catheter, said sensing pressure comprising sensing a venous pressure waveform including at least one of a V pressure wave, generated by filling of the right atrium, and an A pressure wave, generated by contraction of the right atrium;
   receiving an ECG signal;
   measuring a propagation delay of said venous pressure waveform using a processor, said measuring comprising employing an R wave of said ECG signal as a fiducial point with respect to which said propagation delay is measured; and
   employing said propagation delay to provide an indication that said catheter tip is located in said patient at the junction of the superior vena cava (SVC) and the right atrium (RA).

10. A method for accurate placement of a catheter tip in a patient according to claim 9 and wherein said sensing pressure comprises:
    sensing a heart valve opening/closing signal which propagates at approximately 1540 m/sec.; and
    sensing a pressure wave generated by the emptying, filling and contraction of the right atrium which propagates at approximately 2 msec.

11. A method for accurate placement of a catheter tip in a patient according to claim 10 and also comprising distinguishing between said heart valve opening/closing signal and said pressure wave.

12. A method for accurate placement of a catheter tip in a patient according to claim 11 and wherein said indicating comprises calculating a time relationship between said heart valve opening/closing signal and said pressure wave.

13. A method for accurate placement of a catheter tip in a patient according to claim 9 and also comprising displaying catheter tip insertion instructions on a monitor based at least partially on an output from said indicating.

\* \* \* \* \*

UNITED STATES PATENT AND TRADEMARK OFFICE
CERTIFICATE OF CORRECTION

PATENT NO. : 8,715,195 B2
APPLICATION NO. : 12/594869
DATED : May 6, 2014
INVENTOR(S) : David Ziv It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 928 days.

Signed and Sealed this

Twenty-ninth Day of September, 2015

Michelle K. Lee
*Director of the United States Patent and Trademark Office*